United States Patent [19]
Paulsen

[11] Patent Number: 5,428,997
[45] Date of Patent: Jul. 4, 1995

[54] METHOD OF AND DEVICE FOR FLUID SURFACE DETECTION USING AN ULTRASONIC TRANSDUCER

[75] Inventor: Mark T. Paulsen, Chanhassen, Minn.

[73] Assignee: Pasteur Sanofi Diagnostics, France

[21] Appl. No.: 917,205

[22] Filed: Jul. 20, 1992

[51] Int. Cl.⁶ .............................................. G01H 1/00
[52] U.S. Cl. ..................................................... 73/579
[58] Field of Search ................. 73/579, 587, 607, 620, 73/622, 633, 290 V; 310/316, 318; 307/264; 331/116 R, 4

[56] References Cited

U.S. PATENT DOCUMENTS

| | | | |
|---|---|---|---|
| 4,275,363 | 6/1981 | Mishiro et al. | 331/4 |
| 4,427,132 | 1/1984 | Thomson | 73/290 V |
| 4,445,064 | 4/1984 | Bullis | 310/316 |
| 4,562,413 | 12/1985 | Mishiro et al. | 331/116 |
| 4,578,650 | 3/1986 | Watson | 331/160 |
| 4,587,958 | 5/1986 | Noguchi et al. | 128/24 A |
| 4,641,053 | 2/1987 | Takeda | 310/317 |
| 4,754,186 | 6/1988 | Choperena et al. | 310/316 |
| 4,937,466 | 6/1990 | Osterkamp et al. | 307/264 |
| 4,977,786 | 12/1990 | Davis | 73/864.24 |

FOREIGN PATENT DOCUMENTS 0079422 5/1983 European Pat. Off. .
0209872 1/1987 European Pat. Off. .
0355038 2/1990 European Pat. Off. .

OTHER PUBLICATIONS

Van Der Burgt, C. M. et al., "Motional Positive Feedback Systems for Ultrasonic Power Generators", IEEE Transactions on Ultrasonics Engineering, Jul. 1963, pp. 2–19.

Neppiras, E. A., "Motional Feed-back Systems for Ultrasonic Transducers".

Bullis, Davis C., et al., "Response of Ultrasonic Motional Bridge Circuits Under Resistive and Reactive Loads", IEEE Transactions on Sonics and Ultrasonics, vol. SU-29, No. 2, Mar., 1982, pp. 92–97.

Primary Examiner—Richard E. Chilcot, Jr.
Assistant Examiner—William L. Oen
Attorney, Agent, or Firm—Fredrikson & Byron

[57] ABSTRACT

The present invention provides a method of detecting a fluid surface and a circuit for an ultrasonic transducer for detecting such a fluid surface. In accordance with the method, an ultrasonic transducer driver generates a first voltage proportional to the resonant frequency of the ultrasonic transducer. A reference voltage is generated and the reference voltage and the first voltage are monitored and compared, and a surface detect signal is generated when the first voltage drops below the reference voltage. The circuit of the invention includes means for generating a first voltage proportional to the resonant frequency of the transducer, means for generating a reference voltage, and a comparator for monitoring the first and reference voltages and generating a surface detect signal when the first voltage drops below the reference voltage.

2 Claims, 3 Drawing Sheets

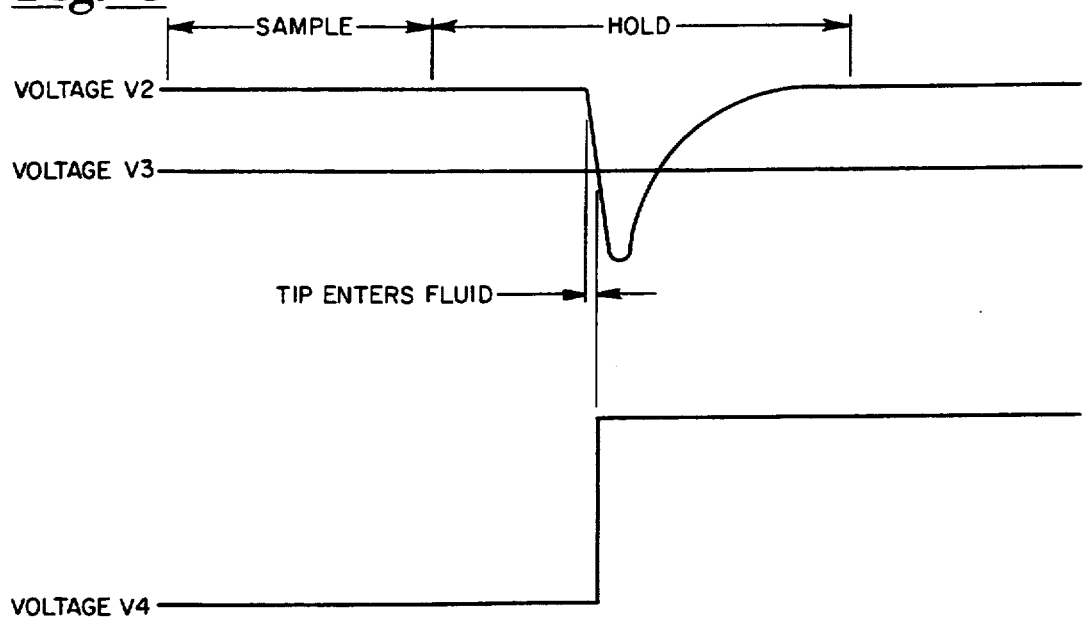
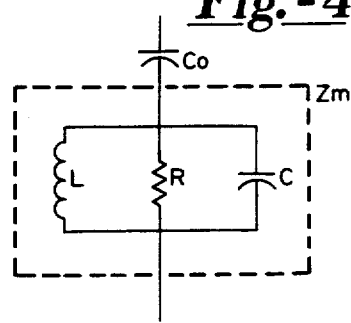
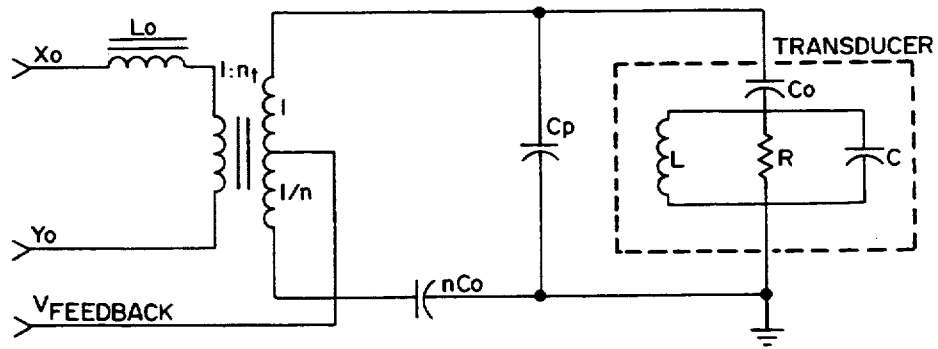

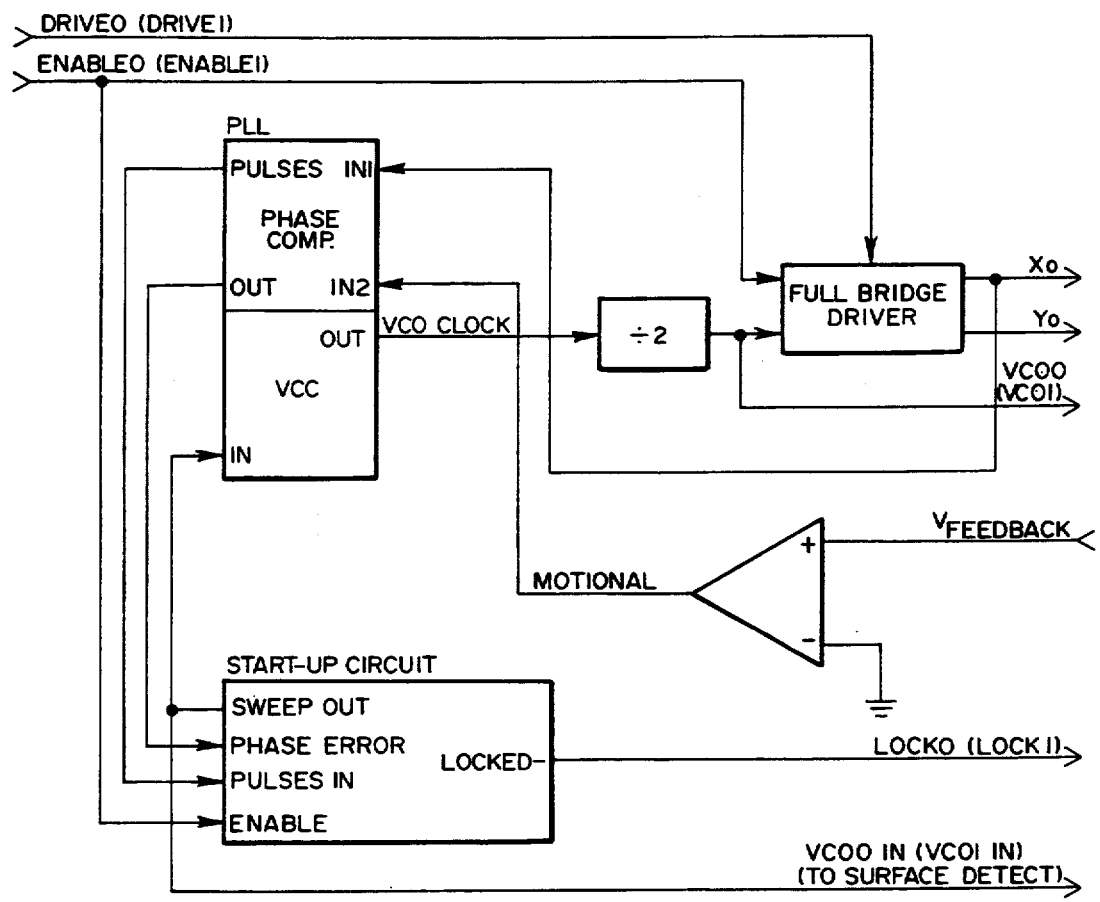
Fig.-6 FULL BRIDGE DRIVER

5,428,997

METHOD OF AND DEVICE FOR FLUID SURFACE DETECTION USING AN ULTRASONIC TRANSDUCER

FIELD OF THE INVENTION

The invention relates to fluid surface detection devices and methods and particularly relates to methods and circuits using ultrasonic transducers for fluid surface detection.

BACKGROUND OF THE INVENTION

Ultrasonic vibratory probes have been used in automated chemical analyzers where a probe is used to automatically withdraw liquid from a vessel containing liquid samples or reagents. Robotic probes of other types have been similarly used in such instruments.

In automated analyzer systems, it is desirable for the probe element to be able to detect the surface of the liquid so the probe's contact with the vessel's contents is minimized, thus, decreasing the possibility of carry over of liquid on the probe.

Various types of level sensors have been developed to provide such surface or level detection. One type of level sensor used with robotic probes in chemical analyzers are referred to as capacitive level sensors. They operate on the principle that every conductor exhibits a finite electrical capacitance. When a probe having a capacitive level sensor touches a liquid, the higher dielectric constant and greater surface area of the liquid results in an increased probe capacitance that can be detected.

Among prior art capacitive liquid level sensors is the sensor described in Davis U.S. Pat. No. 4,977,786. The sensor disclosed therein is useful in a liquid pipetting system that includes an oscillator coupled to a pipette probe for applying a high frequency signal to the probe, the amplitude or phase of the oscillator being affected by the capacitance of the probe and comparator means that generates a level sensor signal according to the amplitude or phase of the oscillator to signal when the probe reaches the liquid surface. The probe also includes means used to vary the frequency of the oscillator in a repetitive manner.

It is desirable in automatic chemical analyzers systems to use an ultrasonically activated pipetting probe that may perform several functions including reagent mixing and level sensing. It is therefor desirable for the ultrasonic probe to also be able to detect the fluid surface in vessels containing reagents and sample.

SUMMARY OF THE INVENTION

The present invention relates to an electrical circuit and method for providing an ultrasonic pipetting probe with surface detect capabilities. The method of the invention includes the steps of providing an ultrasonic transducer driver that generates a first voltage proportional to the resonant frequency of the ultrasonic transducer, generating a reference voltage, monitoring and comparing the first voltage to the reference voltage, and generating a surface detect signal when the first voltage drops below the reference voltage.

In another embodiment of the invention a circuit is provided for providing an ultrasonically activated pipetting probe with surface detect capabilities. The circuit includes first voltage generating means for generating a first voltage proportional to the resonant frequency of the oscillations of the ultrasonic transducer, means for generating a reference voltage, comparator means for monitoring the first and reference voltages and generating a surface detect signal when the first voltage drops below the reference voltage and a switch that changes status in response to the surface detect signal.

In a preferred embodiment of the invention, the circuit further includes means for removing substantially all DC components from the first voltage and amplification means to amplify the voltage to a level that is detectable above the system noise. Differentiation of the first voltage to remove the DC components allows the circuit of the invention to be used in connection with any ultrasonic transducer circuit board without the necessity of adjusting the circuit to conform to the variations in levels of DC components that occur between different circuit boards.

BRIEF DESCRIPTION OF THE DRAWINGS

FIG. 3 is a graphical representation showing waveforms of voltage from the circuit of FIG. 2;

FIG. 4 is a schematic circuit diagram of an ultrasonic probe for use with the invention;

FIG. 5 is a schematic circuit diagram of a motional bridge for use with the invention; and FIG. 6 is a schematic circuit diagram of a phase locked loop for use with the invention.

DETAILED DESCRIPTION OF THE INVENTION

Figure 1:
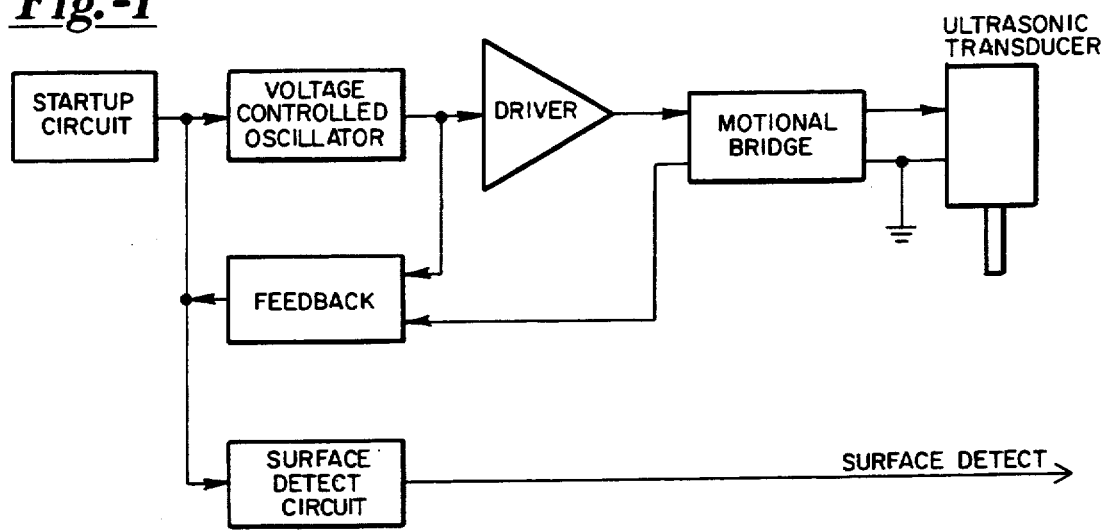
FIG. 1 is a block diagram of an ultrasonic transducer circuit board showing a surface detect circuit.

The resonant frequency of an ultrasonic transducer changes under certain loads. In particular, when the tip of the transducer contacts the surface of a fluid, this frequency will change slightly. Reference is now made to the drawings in which FIG. 1 illustrates a typical ultrasonic transducer probe 10 driven by a startup circuit, voltage controlled oscillator, driver circuit, and motional bridge circuit of conventional design.

Ultrasonic transducers are commonly driven at a resonant frequency at which the electromechanical conversion efficiency is the highest. The resonant characteristic of an ultrasonic transducer presents such a high Q that a small shift in the driving frequency from the resonant frequency causes a significant reduction of the vibration producing efficiency. For this reason, various automatic tracking devices that automatically track the resonant frequency of the transducer to drive the transducer into oscillation, such as a vibration feedback type oscillator and a phase locked loop type oscillator, have been developed and are commonly used.

A circuit of the invention includes first voltage generating means for generating a first voltage proportional to the resonant frequency of the ultrasonic transducer. First voltage generating means useful with this invention may be any means for generating voltage proportional to the resonant frequency such as a voltage controlled oscillator (VCO) that tracks the resonant frequency of the transducer using a circuit such as a motional bridge to provide an electrical feedback signal representative of the oscillating frequency of the transducer. Motional bridge circuits are well known and can be configured in different forms. Motional bridge circuits produce an electrical signal proportional to both the mechanical oscillation frequency and amplitude of an ultrasonic transducer. Various motional bridge circuit designs are described in Neppiras, E. A., "Motional Feed-Back Systems For Ultrasonic Transducers." 1971 *Ultrasonic Conf. Papers*, IPC Science & Technology Press, pages 56–58 (1971), the disclosure of which is incorporated herein by reference.

A schematic diagram of a transducer used with an ultrasonic probe useful with the invention is shown in FIG. 4 where Co is the electrical impedance of the probe and Zm is the electrical equivalent of the mechanical resonance. A motional bridge circuit useful with the invention will substantially nullify the effects of the capacitance Co leaving only the signal from Zm. FIG. 5 shows a simplified version of a motional bridge useful with the circuit and method of the invention. A capacitor, Cp is included in parallel with the transducer on an ultrasonic driver board to help damp out cable capacitance and to provide a load if the ultrasonic probe is disconnected while power is on. This capacitor is not a necessary part of the basic motional bridge, and it will not be referred to in the following description.

The transformer is a step-up transformer and it helps limit the voltage required on the primary. Capacitor nCo has the same scaling as the feedback tap on the transformer. Since the low side of the probe is grounded, the voltage across nCo is out of phase with the feedback voltage. This cancels the effect of Co and makes the feedback voltage proportional to the mechanical oscillation(Zm). The inductor Lo is included to form a series resonance with Co and nCo to make the load seen by Xo-Yo look resistive.

The motional bridge circuit may be closed with a phase locked loop. The ultrasonic probe typically oscillates at a known frequency under fixed conditions. Under any kind of a reactive load, however, the resonant frequency of the mechanical tank circuit will change. Temperature variations and other factors can also affect the resonant frequency. This requires a driver circuit that will track the frequency of the probe under any perceived load and environmental condition.

FIG. 6 diagrams a circuit useful with the surface detect circuit of the invention. When the motional bridge is tuned correctly, the correct frequency of oscillation occurs when the phase difference between the drive signal (Xo) and the feedback is approximately zero. The phase locked loop (PLL) will adjust the frequency until the rising edges of the phase comparator inputs are aligned (no phase error). This should lock the probe at the right frequency, since the MOTIONAL signal is the feedback and Xo is the drive. Once the loop is locked, any change in the feedback frequency will cause a corresponding change in the drive frequency. This allows the system to operate under various loads without losing lock. It is known in the art that an ultrasonic probe will frequently have more than a single resonant frequency and it is important that the phase locked loop focus in on a single resonant frequency rather than switching from one to another during operation. Methods for initiating an ultrasonic probe and a phase locking loop are known in the art and need not be discussed in any detail here.

Desirably, when the ultrasonic transducer is used in an automated chemical analyzer with a probe, a driver circuit will be associated with the VCO and motional bridge for driving the mechanical oscillation frequency of the transducer in response to signals from the feedback system. Desirably, a bipolar full bridge driver such as a L298 driver, commercially available from various sources such as SGS-Thomson, France, able to operate with a supply voltage as low as 5 V will be used. If necessary or desired, the output drive level to the motional bridge can be varied.

Figure 2:
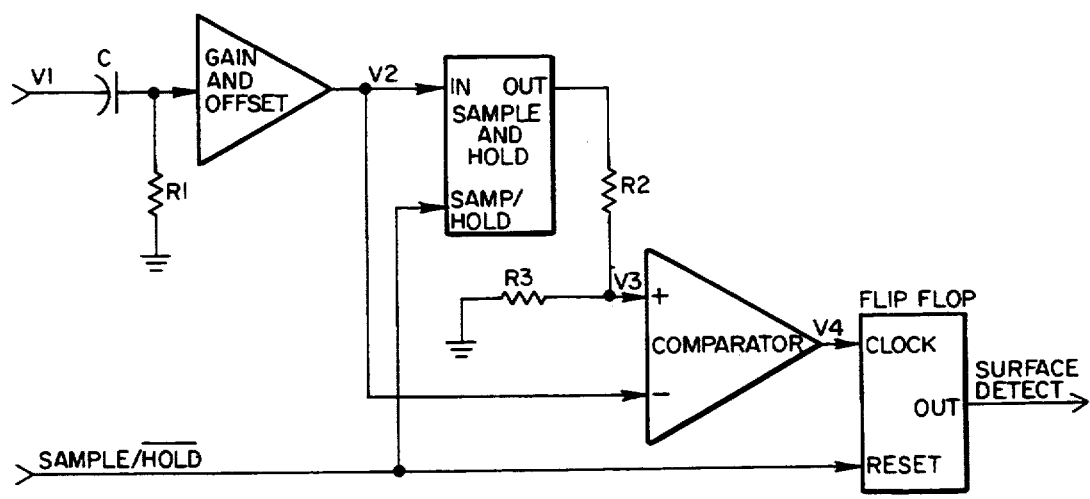
FIG. 2 is a circuit diagram showing a preferred embodiment according to the present invention.

In an embodiment of this invention, the frequency change can be measured at the input to the phase locked loop VCO. FIG. 2 shows a circuit useful in making the measurement. As described above, the method of the invention includes the step of generating a first voltage that is directly proportional to the resonant frequency of the ultrasonic transducer. The measured frequency shift is likely to be very small in the range of about 20 Hz which corresponds to a negative voltage shift of 100 mV.

In a preferred embodiment, the first voltage V1 generated by the transducer is differentiated by capacitor C and resistor R1 as shown in FIG. 2 to remove any DC component of the signal. The capacitor and resistor may be of any common type sufficient to substantially filter the DC component from the signal, acting as a high pass filter. Since the break frequency of the signal will vary with the speed of the probe, the capacitor and resistor should be chosen so that low frequency and DC components will be screened out. A capacitor C of 0.47 microfarads and a resistor R of 47 kOhms have been shown to serve this purpose in a circuit of the invention. The resulting AC voltage is then amplified to a detectable level and an offset is added to provide a known DC level to the signal to generate voltage V2. Adding a gain of about 20 and offsetting the voltage by an amount approximately equal to one-half the supply voltage to the sample and hold amplifier (described below) has been used advantageously with a circuit of the invention.

As described above, the circuit and method of the invention further include means for generating a reference voltage. Desirably, this reference voltage is generated by a sample and hold (S/H) amplifier of a type which is commercially available. Preferably, the S/H amplifier will include a discrete capacitor capable of holding a substantially constant reference voltage for a period of time longer than that required for the ultrasonic transducer to detect the fluid surface, e.g. up to a second or more. The S/H amplifier desirably will provide a substantially constant voltage between about 2 and about 12 volts; the S/H amplifier of the circuit depicted in FIG. 2 is optimally provided with a supply voltage of about 12 volts.

In one preferred embodiment of the invention, depicted in FIG. 2, the sample and hold amplifier samples the voltage V2 as the transducer tip approaches the fluid surface. At some time prior to the tip entering the fluid the S/H is put into a hold mode which holds a constant voltage substantially equal to voltage V2 at the time the hold cycle of the S/H amplifier is initiated. Since the voltage output of the S/H amplifier is substantially the same as the sampled voltage V2, this voltage is used as the reference voltage to which the scaled voltage of the VCO is compared. When the probe tip contacts the fluid surface, the first voltage (V2) spikes and this spike is what is intended to be detected by the comparator means. However, the reference voltage must be at a level which will avoid a false surface detect signal resulting from slight changes in voltage caused by noise in the circuit. In the embodiment of FIG. 2, this is accomplished by using resistors R2 and R3 to form a resistor divider and drop the voltage level of the S/H output to provide the reference voltage V3 of the invention. It is to be understood, though, that any suitable means of providing an offset to the reference voltage can be used.

Comparator means of the invention monitor the first and reference voltages and when the first voltage drops below the reference voltage, the comparator means produces a surface detect signal. Voltage comparators are well known in the art; voltage comparator means useful in the invention can be selected from a range of commercially available voltage comparators.

In one useful embodiment, the circuit of the invention further includes a switch that changes status in response to the surface detect signal. The switch can be any known type of switch, but a "flip flop" has been found to serve particularly well. Flip flop switches are commercially available. The flip flop used in the invention should obviously be chosen such that it is appropriate for the power supply being used; a 4013 flip flop has been found to serve its intended function.

The comparator means monitors and compares the reference voltage to the first voltage (or, as shown in FIG. 2, a voltage V2 which is proportional to the first voltage V1). When the ultrasonic transducer contacts the surface of the fluid the first voltage will be a voltage spike as shown as V2 in FIG. 3. When the voltage spike occurs, the tip has entered the fluid and the voltage V2 drops below the voltage V3 as shown in FIG. 3. The comparator's output then goes to a logic high state and triggers the flip flop switch to signal a "surface detect". The surface detect signal will remain in a triggered state until the S/H is put into the sample mode. This resets the flip flop to do another surface detect.

Another possible method of detecting a fluid surface using an ultrasonic transducer would measure the power delivered to the transducer by sampling the ultrasonic transducer current. This method uses the principle that the impedance of the ultrasonic transducer changes when it contacts a load, such as fluid. This impedance change causes a change in the ultrasonic transducer current when the drive voltage is constant. I found this method to present several problems in attempting to adapt it for use with an ultrasonic transducer used in connection with a pipetting probe. One difficulty was the fact that the total current change can be very small (almost unmeasurable) depending on the configuration of the transducer and the size of the load. Also the current waveform is an AC waveform so it would have to be peak detected or rectified to sample the change, which would require a more complex circuit to be used. Another problem with this method is that sampling current usually requires some type of sample resistor to be used which increases the power drive required.

While a preferred embodiment of the present invention has been described, it should be understood that various changes, adaptations and modifications may be made therein without departing from the spirit of the invention and the scope of the appended claims.

What is claimed is:

1. A method of detecting a fluid surface comprising the steps of providing an ultrasonic transducer driver that generates a first voltage proportional to the resonant frequency of the ultrasonic transducer, generating a reference voltage, monitoring and comparing the first voltage to the reference voltage, and generating a surface detect signal when the first voltage drops below the reference voltage.

2. A circuit of an ultrasonic transducer comprising first voltage generating means for generating a first voltage proportional to the resonant frequency of the ultrasonic transducer, means for generating a reference voltage, and comparator means for monitoring the first and reference voltages and generating a surface detect signal when the first voltage drops below the reference voltage.

* * * * *